United States Patent [19]

Bergemann et al.

[11] Patent Number: 4,628,186

[45] Date of Patent: Dec. 9, 1986

[54] HEATER-SCALE FOR HEATING FLUIDS FOR INJECTION INTO A PATIENT

[75] Inventors: David Bergemann, Vernon Hills; Alan A. Figler, Algonquin; Rene Lamadrid, Lake Forest; Stanley Pernic, Round Lake; John J. Selman, Vernon Hills, all of Ill.

[73] Assignee: Baxter Travenol Laboratories, Inc., Deerfield, Ill.

[21] Appl. No.: 676,766

[22] Filed: Nov. 30, 1984
(Under 37 CFR 1.47)

[51] Int. Cl.⁴ .............................................. H05B 1/02
[52] U.S. Cl. ..................................... 219/497; 219/518; 219/492; 219/308; 219/328; 604/114; 177/245
[58] Field of Search .............. 219/497, 518, 309, 499, 219/492, 501, 494, 330, 331, 10.55 B, 328, 302, 308; 177/245, 144; 604/113, 114

[56] References Cited

U.S. PATENT DOCUMENTS

| | | | |
|---|---|---|---|
| 2,561,134 | 7/1951 | Peters | 219/330 |
| 3,114,027 | 12/1963 | Busch et al. | 219/450 |
| 3,191,003 | 6/1965 | Yohe | 219/450 |
| 3,235,709 | 2/1966 | Fischer | 219/450 |
| 3,505,498 | 4/1970 | Shevlin | 219/385 |
| 3,698,494 | 10/1972 | Gaudin | 259/55 |
| 3,786,220 | 1/1974 | Harnden | 219/10.49 |
| 3,870,858 | 3/1975 | Schimke | 219/328 |
| 4,051,346 | 9/1977 | Lenmark | 219/328 |
| 4,165,633 | 8/1979 | Raisanen | 73/76 |
| 4,192,989 | 3/1980 | Jeromin | 219/216 |
| 4,210,216 | 7/1980 | Godden | 177/245 |
| 4,276,948 | 7/1981 | Nichols | 177/245 |
| 4,309,592 | 1/1982 | LeBoeuf | 219/301 |
| 4,314,143 | 2/1982 | Bilstad et al. | 219/497 |
| 4,378,854 | 4/1983 | Rosen | 177/118 |
| 4,481,409 | 11/1984 | Smith | 219/518 |

Primary Examiner—M. H. Paschall
Attorney, Agent, or Firm—Paul C. Flattery; Daniel D. Ryan; Kay H. Pierce

[57] ABSTRACT

A heater-scale having a curved supporting member upon which a bag of fluid to be heated can be placed, has a distributed two-dimensional heating element affixed to a lower surface thereof. The curved member is supported by a load cell for generating an electrical signal proportional to the weight of the bag on the heater member, a thermistor is in contact with the fluid whose temperature is to be maintained, a thermistor is affixed to the heater member, and a control system senses the weight and temperature of the bag of fluid as well as the temperature of the heater member for the purpose of nonlinearly adjusting the electrical current supplied to the heater element as fluid is removed from or variable temperature fluid is added to the bag so as to maintain the bag at a predetermined temperature.

15 Claims, 7 Drawing Figures

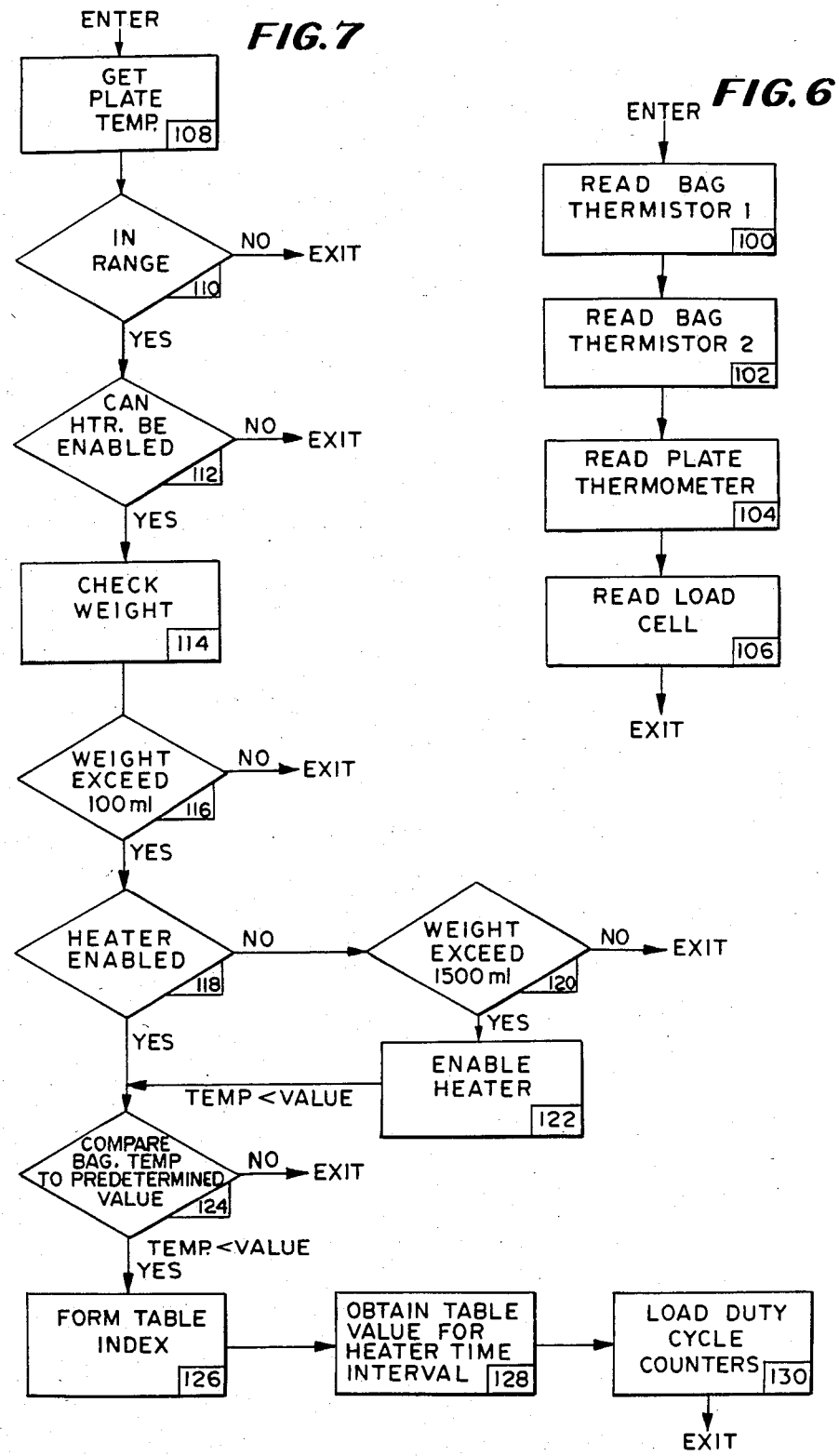

HEATER-SCALE FOR HEATING FLUIDS FOR INJECTION INTO A PATIENT

FIELD OF THE INVENTION

The invention pertains to heater-scales of a type usable to heat and weigh fluids used for bodily injection.

BACKGROUND OF THE INVENTION

Hemo-dialysis is a widely used method of kidney dialysis for treatment of end stage renal disease. In the hemodialysis process a patient's blood is cleansed by passing it through an artificial kidney dialysis machine. This process requires that the patient be physically connected to the machine several times a week so that patient's blood may be transferred to and from the membranes in the machine.

Peritoneal dialysis has been found to be usable with many patients as a more convenient and in many ways desirable alternative to traditional hemo-dialysis. In the peritoneal dialysis process a dialysis solution is infused into the patient's peritoneal cavity using tubing and a catheter. After a given period of time the dialysis solution is removed and replaced.

A peritoneal dialysis apparatus has been disclosed in U.S. patent application Ser. No. 448,450 entitled "Peritoneal Dialysis Apparatus", filed Dec. 10, 1982 and assigned to the assignee of the present application. Such an apparatus discloses therein, and in particular with respect to FIG. 4 thereof, a heater-scale structure usable to continuously heat and to weigh dialysis fluid to be infused into a patient. A similar scale is shown mechanically in FIG. 1 of U.S. patent application Ser. No. 548,390 entitled "Peritoneal Dialysis Apparatus", filed Nov. 3, 1983 also assigned to the assignee of the present application.

A significant problem in peritoneal dialysis heater-scales has been found to lie in the fact that dialysis fluids come in various sizes of bags. Any heater-scale must be usable, with little or no operator intervention, to properly heat bags of different sizes. Additionally, the heater-scale must compensate for the fact that, during a typical dialysis process, the bag will be respectively partially emptied and refilled with fluid of varying temperatures resulting in varying volumes of fluid being heated from different initial temperatures.

SUMMARY OF THE INVENTION

The invention provides for a heater-scale having a shaped means for supporting a selected contained volume of fluid to be weighted and heated, means for continuously sensing the weight of the contained volume of fluid and for generating an electrical signal in response thereto, distributed means for heating affixed to a selected surface of the supporting means, for evenly heating the volume of fluid in response to an electrical signal applied thereto; means for sensing the temperature of the contained volume of fluid and means for controlling the electrical signal applied to the heating means to continuously and evenly heat the contained volume of fluid so as to maintain that volume at a predetermined temperature.

The invention further provides for a heater-scale wherein the supporting means includes a concave supporting surface for receiving the contained volume of fluid and wherein the heating means is affixed to a spaced apart convex surface with the temperature sensing means extending through the two surfaces so as to be in contact with the contained volume of fluid.

The invention also provides means for initially raising the temperature of the contained volume to the predetermined temperature without overshoot, and then for continuously sensing the changing weight of the contained volume. Means are also provided for maintaining the temperature of the variable contained volume at the predetermined value.

In accordance with the present invention, a method is provided for heating a contained volume of fluid including the steps of supporting the contained volume of fluid; continuously monitoring the temperature of the fluid; comparing a predetermined set-point value to the monitored fluid temperature; forming a first time interval; forming a second time interval, shorter than the first time interval and nonlinearly related thereto, in response to a positive difference between the set-point value and the monitored fluid temperature; and applying heat to the fluid only during the second time interval.

BRIEF DESCRIPTION OF THE DRAWINGS

FIG. 6 is a flow diagram illustrating an exemplary sampling sequence for reading information from the heater-scale of the present invention.

FIG. 7 is a flow diagram illustrating an exemplary heater control method usable with the heater-scale of the present invention.

DETAILED DESCRIPTION OF THE PREFERRED EMBODIMENTS

Figure 1:
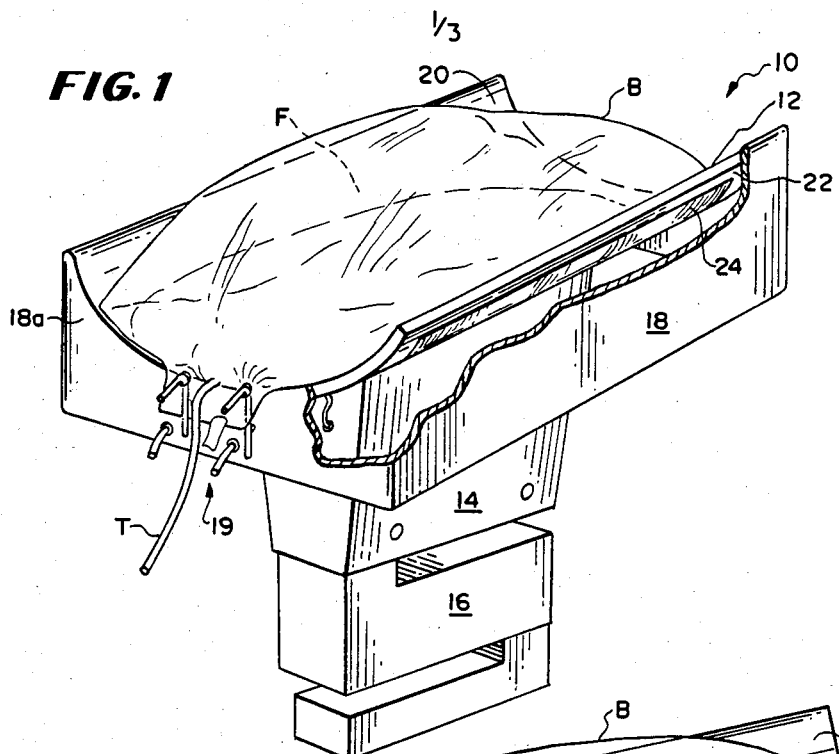
FIG. 1 is a perspective view of a heater-scale embodying the present invention with a portion thereof broken away.

With respect to the figures, FIG. 1 illustrates a heater-scale 10 supporting a volume of conventional peritoneal dialysis fluid F in a bag B. The fluid F is to be simultaneously heated and weighed. The scale 10 includes a concave shaped plate 12 upon which the bag B of fluid F is placed. The plate 12 is supported by a bracket 14 which in turn is connected to a platform load cell 16. The platform load cell 16 produces an output voltage proportional to the weight of the contained fluid F placed on the plate 12. A housing 18, shown partly broken away in FIG. 1 partially encloses the plate 12.

The bag B is placed on an upper concave surface 20 of the plate 12 for weighing and heating. Standard sizes for the bag B are 2 liter, 3 liter and 5 liter volumes. Tubing T provides a conduit drawing the fluid F from or supplying fluid to the bag B. A clip 19 holds the flexible tube T against a front panel 18a of the housing 18. The purpose of the spring clip 19 is to retain the tubing T in a fixed relationship relative to the bag B as the fluid F is drained from or pumped to the bag B.

Affixed to a lower convex surface 22 of the plate 12 is a distributed heater 24. The volume of fluid F on the plate 12 can be reduced or increased during the time interval it is being heated and weighed, by the removal or addition of fluid F through the attached tube T.

An important advantage of the heater-scale 10, lies in the fact that the various volumes of fluid F are all properly maintained at or near normal body temperature. Proper heating temperature is maintained irrespective of which size bag B is initially placed on the scale 10 and irrespective of whether or not that volume is reduced over a period of time by a net withdrawal of fluid F therefrom.

Another important aspect of the present invention resides in the use of the platform type load cell 16. The bag B has a center of gravity whose position varies relative to the plate 12. The load cell 16 will produce an electrical output which is independent of any off center loading of the bag B. This is especially important, because the center of gravity of the bag B will change as the remaining volume of fluid F is decreased or as the bag B is refilled with fluid F.

Figure 2:
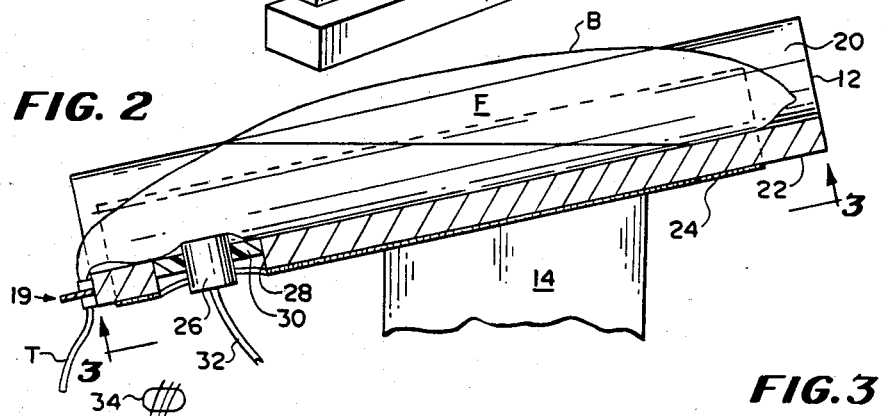
FIG. 2 is a side view of the scale of FIG. 1 in section showing the relationship of the electrical and mechanical components.

FIG. 2 is a view in section of the scale 10 of FIG. 1 and illustrates the relationship between the shaped support member 12 and the distributed electrical heater element 24 affixed to the lower convex surface 22 thereof. FIG. 2 also illustrates a fluid temperature sensor 26, which includes a pair of thermally coupled thermistors. The sensor 26 is supported in an opening 28 in the plate 12 by a disk 30 of thermal insulating material. The temperature sensor 26 extends slightly above the upper surface 20 of the plate 12 so as to be in direct contact with the bag B of contained fluid F. An electrical cable 32 is connected to the dual thermistors in the package 26. When biased with a constant voltage of 0.85 volts DC, the thermistors 26 provide a temperature dependent current in a range of 0.06 milliamps to 0.47 milliamps DC on the cable 32.

Figure 3:
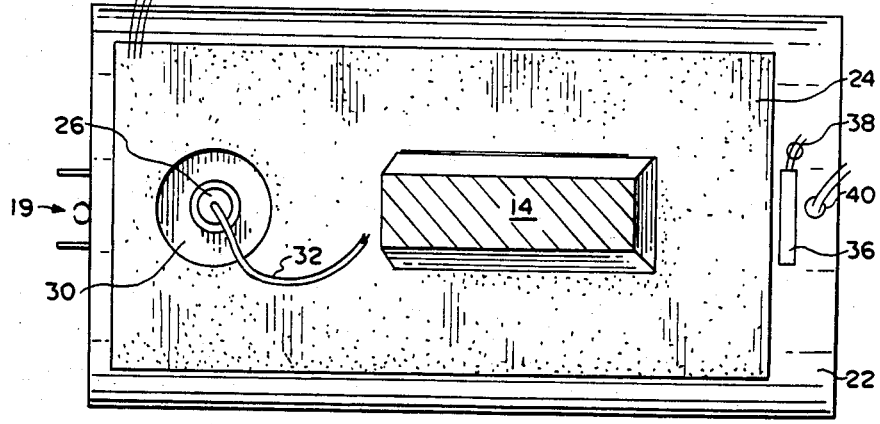
FIG. 3 is a bottom plan view taken along line 3—3 of FIG. 2 illustrating the lower surface of the scale.

FIG. 3 is a bottom view of the plate 12 of the heater-scale 10 and illustrates the distributed heater element 24 affixed to the lower curved surface 22. As can be seen from FIG. 3 the heater element 24 occupies a substantial area of the lower surface 22 of the plate 12. It has been found that if the heater element 24 is a 500 watt heater operated at either 120 volts, or 240 volts that preferably it should be on the order of 9¼" wide by 10¼" long. Additionally, it is preferred that the heater element 24 be formed of low leakage resistance wire essentially uniformly distributed therein.

Cables 34 provide for either a 120 volt input or a 240 volt input to the heater 24. A plate temperature sensing thermistor 36 is affixed to the lower surface 22 of the plate 12 for the purpose of continuously monitoring the temperature of the plate 12. Current variations through the element 36 as the temperature of the plate 12 changes can be sensed on the lines 38. Additionally the plate 12 includes a thermal fuse 40 for safety purposes. If the temperature of the plate 12 exceeds 56° C., the fuse 40 will open circuit shutting off the heater current on the lines 34.

Figure 4:
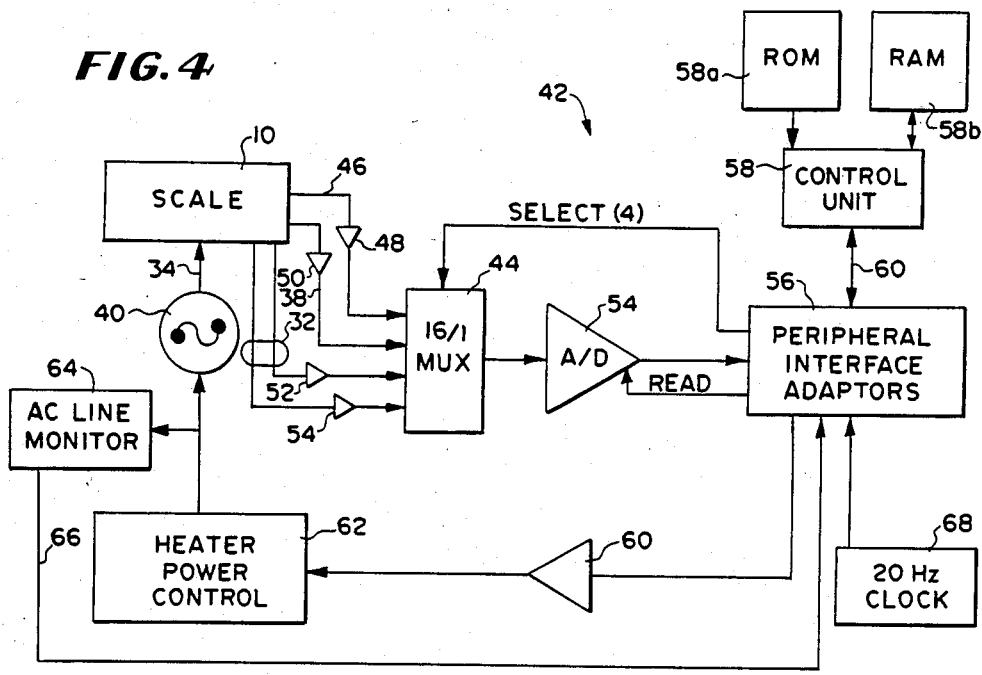
FIG. 4 is a schematic block diagram of a control system usable with the heater-scale of the present invention.

FIG. 4 illustrates a schematic block diagram of a control system 42 usable with the scale 10. The control system 42 includes a 16 to 1 analog multiplexer 44. The multiplexer 44 receives analog signals from the scale 10. A line 46 connects the load cell 16 of the scale 10, for the purpose of transmitting a voltage generated in the load cell 16 corresponding to the weight of the bag B, to a conventional operational amplifier 48 whose output is in turn one of the inputs to the multiplexer 44. The line 38 transmits electrical signals from the plate thermistor 36 from the scale 10 to a thermistor amplifier 50. The output from the plate thermistor amplifier 50 is an input to the multiplexer 44. The cable 32 transmits electrical signals from the bag temperature thermistors 26 to respective thermistor amplifiers 52, 54. The outputs of the thermistor amplifiers 52, 54 in turn become inputs to the analog multiplexer 44.

An output of the multiplexer 44 is connected to an analog-to-digital (A/D) converter 54, which is in turn connected to peripheral interface adaptor (PIA) 56 of a conventional type. Lines from the PIA 56 provide a READ signal to the converter 54 and select signals to select a multiplexer channel in the multiplexer 44. The PIA 56 is in turn connected to a control unit 58 by a bidirectional communications bus 60. The control unit can for example be a programmable Motorola type 6802 microprocessor.

The control unit 58 is in turn connected to a read only memory 58a (ROM) and to a random access memory 58b (RAM). A control program to control the temperature of the scale 10 can be stored in the ROM memory 58a. The RAM 58b can be used to temporarily store scale readings or other variable information.

An output line of the PIA 56 is connected via an amplifier 61, to a heater power control unit 62 which can be an optically isolated OPTO 22 type solid state relay. The heater power control unit 62 is in turn connected through the fuse 40 by the lines 34 to the heater element 24.

An AC Line Monitor 64 of a conventional type is electrically connected to the output of the heater power control unit 62. The monitor 64 continuously monitors the electrical signal being supplied to the heater 24. An output signal from the monitor 64 on a line 66 enables the control unit 58 to monitor whether or not power is being supplied to the heater 24. As is discussed in more detail subsequently, during certain predetermined time intervals, the power to the heater 24 should be turned off. By checking the signal on the line 66 the control unit 58 can verify that, during predetermined time intervals, power to the scale 24 is being turned off.

A real-time clock 68 which generates a 20 hertz signal that provides interrupt pulses to the control unit 58 via the PIA 56. These interrupt pulses, 50 milliseconds apart provide a real-time signal usable by the control unit 58 to count timers and to keep track of heater control time intervals as discussed subsequently.

As discussed in more detail subsequently, fluid temperature signals on the lines 32, scale weight signals on the line 46 and plate temperature signals on the line 38 are digitized in the converter 54 and then sensed by a control program in the ROM memory 58a. The control unit 58, in combination with the control program in the ROM memory 58a, generate output signals to be transferred through the heater power control unit 62, so as to properly maintain the temperature of the bag B of fluid F on the scale 10.

Figure 5:
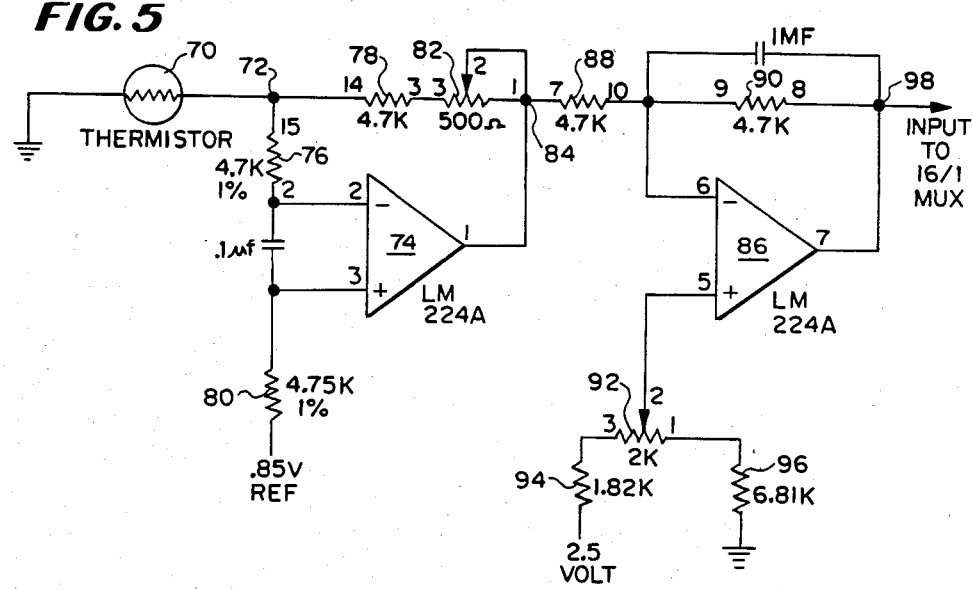
FIG. 5 is a schematic diagram of a thermistor amplifier usable with the heater-scale of the present invention.

FIG. 5 illustrates a schematic view of a thermistor amplifier corresponding to each of the amplifiers 50, 52 or 54. A thermistor 70 corresponding to either of the bag thermistors 26 or the plate thermistor 36 is coupled between electrical ground and an input node 72 to an operational amplifier 74. The operational amplifier 74 has a bias compensation resistor 76, and a feedback resistor 78 of equal value 4.7K ohms. A second bias compensation resistor 80 is coupled to a 0.85 volt reference voltage. A 500 ohm potentiometer 82 provides a gain adjustment point in the feedback path of the amplifier 72.

An output node 84 of the amplifier 74 is electrically connected to a second operational amplifier 86, through a 4.7K ohm input resistor 88. The amplifier 86 has a feedback resistor 90 which has the same value, 4.7K ohms, as does the input resistor 88. An offset potentiometer 92 is coupled between a 1.82K ohms resistor 94 that is returned to a 2.5 Volt d.c. reference and a 6.81K ohm resistor 96 that is returned to electrical ground. The potentiometer 92 is adjusted for a zero volt output on an output node 98 at a temperature sensed by the thermistor 70 of 3° C.

The potentiometer 92 is adjusted to provide zero volts ouput at the node 98 for a 3° sensed temperature, as a safety consideration to ensure that the fluid F is not frozen.

The amplifiers 52 and 54 are implemented preferably with a type LM 224A quad amplifier package. Each of the four operational amplifiers, such as 74, 86, are formed in one package to provide for minimal temperature tracking errors between the two amplifiers 52, 54. Preferably, the 4.7K ohm resistors, such as the resistors 76, 78, 88, 90 for both amplifiers 52, 54 are also all formed in a single package for the same reason.

FIG. 6 illustrates a flow diagram for sampling the signals measurable off of the scale 10. The flow diagram of FIG. 6 could readily be implemented by one of skill in the art in a program stored in the ROM memory 52. The flow diagram of FIG. 6 could be implemented as either an interrupt driven program that responds to interrupts generated by the 20 hertz interrupt clock 68 or could be called on a regular basis using standard polling techniques.

When the program corresponding to the flow diagram of FIG. 6 is first entered, in a step 100, a reading is made by the analog-to-digital converter 54 of the signal off of one of the two bag temperature termistors 26. Subsequently, in a step 102, a reading is made by the analog-to-digital converter 54 off of the second of the two bag temperature thermistors 26. A reading is then made, in a step 104, off of the plate temperature thermistor 36. Finally, in a step 106, a signal from the load cell 16 indicating the weight of the fluid F on the plate 12 is read. The flow diagram of FIG. 6 is then exited.

In normal operation it has been found desirable to make a set of sample readings as indicated in FIG. 6 every three seconds. The temperature and weight readings can then be processed for the purpose of controlling the signals applied to the heater 24. The three second sample time intervals are measured using pulses from the interrupt clock 68.

For purposes of making the scale measurement, it has been found desirable to scale the voltage off of the load cell 16 such that 3 digital counts correspond to each cubic centimeter of volume of fluid F in the bag B.

A flow diagram for an exemplary control program for use with the control system 42 is illustrated in FIG. 7. A control program based on the flow diagram of FIG. 7 could be directly implemented by one of skill in the art and stored in machine language form in the ROM 52. The control program illustrated in FIG. 7, operates on the same 3 second base period as does the sampling sequence of FIG. 6. The sampling program of FIG. 6 could be implemented preferably as an interrupt driven program that runs simultaneously with the control program of FIG. 7.

Using standard interrupt handling routines and techniques, the control unit 58 counts a period of 3 seconds as represented by 60 interrupt pulses from the clock 68. During a first 3 second period, samples are collected from the scale 10 in accordance with the flow diagram of FIG. 6. The samples are then processed, as discussed subsequently and as illustrated in FIG. 7. The control unit 58 utilizes the processed results to determine how long during the next 3 second interval, power should be applied to the heater 24 through the heater power control unit 62.

It should be noted that one of the advantages of the present apparatus results from the discontinuously applied power to the heater 24. The control system 42 is always able to determine when, during a given 3 second period, power should not be applied to the load. The output from AC line monitor 64 can be interrogated during this time period, to verify that in fact the power to the heater 24 has been turned off by the heater power control 62.

A further advantage that results from the use of discontinuously applied AC power is that the heater 24 will heat 2 liter, 3 liter, or 5 liter bags of fluid quickly to 37° C. without overshoot.

Heating time intervals to heat respective volumes from room temperature (20° C.) to 32° C., the minimum temperature at which fluid F can safely be delivered to a patient are on the order of 20 minutes.

With respect to FIG. 7, in an initial step 108 the control unit 58 checks the temperature of the plate 12 to determine that the plate 12 has not exceeded a temperature of 50° C. If the plate temperature exceeds 50° C. the control unit in a step 110 can make an error branch to set a flag or visual indicator signaling that the plate temperature is excessive.

If the temperature of the plate 12 is not excessive, the control unit 58, in a step 112, can check for other conditions that might make it undesirable to turn on the heater 24. In a dialysis environment, such conditions can include cases where the system 42 is not in an operating step that requires the heater 10 to be energized. Alternately, if the system 42 is in an alarm state or at the end of a treatment, or if the bag thermistor readings differ by more than a predetermined amount, turning on the heater 10 could be undesirable.

In a step 114, assuming the heater 24 can be enabled, the control unit 58 can check the actual weight of the bag B. If the weight of the fluid F does not exceed the equivalent of 100 ml of volume, the control unit 58 exits, at a step 116, due to a failure of the fluid volume to exceed this threshold.

In a step 118 the control unit 58 can determine if the heater 24 had previously been enabled. The test for heater enablement, absent any other error conditions, is whether or not the bag of fluid even had a sensed volume in excess of 1500 ml. If the heater 24 has not been enabled, the control unit 58 in a step 120 compares the sensed volume of fluid F to a second threshold of 1500 ml. If the sensed volume does not exceed this second threshold, the control unit 59 exits. If the sensed volume of fluid F exceeds 1500 ml, in a step 122 the control unit sets the enable heater flag.

In a step 124 the control unit 58 compares the bag temperature to a predetermined value of 37° C. corresponding to normal body temperature. If the actual bag temperature is less than 37°, the control unit in a step 126 subtracts the actual bag temperature from the setpoint or predetermined value to form an index pointer for Table 1. T,0170

Table 1 illustrates an empirically derived, non-linear relationship between the error, the amount the set-point exceeds the actual bag temperature and the number of counts, out of 60, that the heater 24 should be energized during the next 3 second period. Each count corresponds to a 50 millisecond period generated by the interrupt clock 68.

The left column, right-portion, in Table 1 illustrates the number of counts out of 60, such as 8, that the heater 24 should be energized for a given temperature difference shown in the right column of Table 1, such as 1 degree between set-point of 37° C. and actual temperature of 36°. The relationship of Table 1 has been optimized for 2 liter, 3 liter and 5 liter bags of standard peritoneal dialysis fluid. One of the advantages of the present apparatus is the ease with which the heating time intervals can be varied to take into account other volumes or other types of solutions.

It should be also noted, that the relationship of Table 1 is non-linear. Surprisingly, when the bag is very cold, with more than 22° C. to warm only a limited amount of heat is applied. In this situation, energy is only applied to the heater 24 for 20 counts out of 60 to prevent overheating of the plate 12 due to the large potential temperature differentials between the plate 12 and fluid F. When the bag of fluid F has been warmed to within 22° C. of the setpoint, power can be applied to the heater 24 for a substantially greater time period, 43 counts out of 60.

Limiting of the time interval that energy is applied to the heater 24 as in Table 1 results in the plate 12 not being heated above 50° C. This not only saves energy, but avoids inadvertent operator burns due to contacting a very hot scale plate.

Again, with reference to FIG. 7, in a step 128, once the index pointer has been formed in step 126, the appropriate number of counts will be retrieved from the appropriate location in Table 1. The counts can then be loaded into duty cycle counters. One counter can be used to set the heater power-on time interval during the next 3 second control interval. The second counter times the control interval. The two counters are preferably locations in the RAM memory 58b whose contents are counted up or down by pulses from the clock 68. Alternately, the counters could be implemented as two special hardware counters.

Modifications and variations of the present invention are possible in light of the above teachings. The broader aspects of the invention can include the use of different heater power control tables. Separate tables could be used for each initial volume of fluid to be heated. The broader aspects of the invention also include non-linear relationships other than the one illustrated in Table 1 or the use of control intervals other than the two and three second intervals discussed herein. The present invention also includes the use of alternate electronic components including hard-wired control units. It is therefore to be understood that within the scope of the appended claims the invention may be practiced, otherwise than as specifically described.

What is claimed and desired to be secured by Letters Patent of the United States is:

1. A heat-scale comprising:
    means for supporting a selected contained volume of fluid to be weighed and heated including a first generally horizontal concave supporting surface for receiving the contained volume of fluid with said heating means affixed to a second, spaced apart, surface thereof and including temperature sensing means extending through said first and second surfaces toward the contained volume so as to be in contact with the contained volume of fluid;
    distributed means affixed to a selected surface of said supporting means for evenly heating the volume of fluid in response to an electrical signal applied thereto;
    means for sensing the temperature of the contained volume of fluid and for comparing the sensed temperature to a predetermined temperature;
    means for switching the electrical signal to said heating means on and off for selected, time intervals which vary nonlinearly with respect to the comparison between the sensed temperature and the predetermined temperature to evenly heat the contained volume of fluid to said predetermined temperature without overshoot and to maintain said volume at the predetermined temperature;
    means for comparing an electrical signal corresponding to a sensed initial weight of the contained volume of fluid to a first predetermined threshold and for enabling said switching means provided said sensed initial weight exceeds said first threshold; and
    means for continuously monitoring said electrical signal applied to said heating means and for interrupting said switching on of said signal in response to sensing a selected condition.

2. A heater-scale as defined in claim 1 wherein said means for comparing further compares an electrical signal corresponding to a continuously variable weight of the contained volume of fluid to a second predetermined threshold and for enabling said switching means provided said weight of fluid exceeds said second threshold.

3. A heater-scale as defined in claim 2 including means for sensing a temperature of said supporting means and for limiting the electrical signal applied to said heating means in response thereto to prevent possible operator burn.

4. A heater-scale as defined in claim 3 wherein said switching means include means for continuously sensing in a predetermined order electrical signals corresponding to the weight of the contained volume, the temperature of the contained volume and the temperature of said supporting means.

5. A heater-scale as defined in claim 4 wherein said switching means include means for establishing first and second time intervals with said first interval being longer than said second time interval and control means for applying the electrical signal to said heating means for said second time interval.

6. A heater-scale as defined in claim 5 including means for comparing the sensed temperature of the fluid to a predetermined value and for generating a corresponding electrical signal and means for adjusting the duration of the second time interval in response thereto.

7. A heater-scale as defined in claim 6 wherein said adjusting means alters the duration of the second time interval non-linearly in response to the difference between the sensed temperature value and the predetermined value.

8. A heater-scale as defined in claim 6 wherein said adjusting means include means for storing a predetermined sequence of second time intervals and means for accessing a selected second time interval in response to said electrical signal.

9. A heater-scale as defined in claim 8 wherein said fluid temperature sensing means include first and second thermistors.

10. A heater-scale as defined in claim 8 including means for limiting the second time interval so that the sensed temperature of said supporting means does not exceed a predetermined value.

11. A heater-scale as defined in claim 10 wherein said monitoring means include means for generating an indicia indicative of the absence of the heating means electrical signal during a checking time interval between when the second time interval ends and when the first time interval ends.

12. A heater-scale as defined in claim 11 including means for generating an error indicia in the absence of said indicia during said checking time interval.

13. A method of controlling heat to be applied to a contained volume of fluid so as to heat the fluid to a predetermined value without temperature overshoot comprising the steps of:
   supporting the contained volume of fluid on a supporting surface;
   continuously monitoring the temperature of the fluid;
   comparing a predetermined set-point value to the monitored fluid temperature;
   forming a first time interval;
   forming a second time interval, shorter than the first time interval, and non-linearly related to a positive difference between the set-point value and the monitored fluid temperature; and
   applying heat to the fluid only during the second time interval;
   sensing the weight of the contained volume of fluid;
   sampling the temperature of the supporting surface; and
   providing electrical power to the electrical heater only during the second time interval, provided the sensed fluid weight exceeds a predetermined threshold and the temperature of the supporting surface does not exceed a predetermined value.

14. A method of control as defined in claim 13, wherein an electrical heater applies heat to the contained volume of fluid including:
   monitoring the electrical power to verify that said power is not being applied to the heater between the end of the second time interval and the end of the first time interval.

15. A method of control as defined in claim 14 wherein:
   sampling of the continuously monitored fluid temperature occurs at predetermined time intervals, the second time interval being shorter when the positive difference is greater than or equal to a fixed value than when the positive difference is less than the fixed value.

* * * * *